United States Patent
Kawano et al.

(10) Patent No.: US 10,415,020 B2
(45) Date of Patent: *Sep. 17, 2019

(54) METHOD FOR PRODUCING NON-ENVELOPED VIRAL PARTICLES

(71) Applicant: TAKARA BIO INC., Shiga (JP)

(72) Inventors: Yasuhiro Kawano, Machida (JP); Shuohao Huang, Toronto (CA); Tatsuji Enoki, Kyotanabe (JP); Masanari Kitagawa, Yasu (JP)

(73) Assignee: TAKARA BIO INC., Shiga (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/540,606

(22) PCT Filed: Jan. 8, 2016

(86) PCT No.: PCT/JP2016/050431
§ 371 (c)(1),
(2) Date: Jun. 29, 2017

(87) PCT Pub. No.: WO2016/111343
PCT Pub. Date: Jul. 14, 2016

(65) Prior Publication Data
US 2018/0273907 A1  Sep. 27, 2018

(30) Foreign Application Priority Data
Jan. 9, 2015 (JP) .................... 2015-002883

(51) Int. Cl.
| | |
|---|---|
| *C12N 7/00* | (2006.01) |
| *C07K 14/075* | (2006.01) |
| *C12N 5/10* | (2006.01) |
| *C12N 7/02* | (2006.01) |
| *C12N 15/09* | (2006.01) |

(52) U.S. Cl.
CPC .............. *C12N 7/00* (2013.01); *C07K 14/075* (2013.01); *C12N 5/10* (2013.01); *C12N 7/02* (2013.01); *C12N 15/09* (2013.01); *C12N 2750/14121* (2013.01); *C12N 2750/14151* (2013.01)

(58) Field of Classification Search
CPC ... C12N 7/00; C12N 5/10; C12N 7/02; C12N 15/09; C12N 2750/14121; C12N 2750/14151; C12N 15/86; C12N 2750/14143; C12N 2750/14043; C12N 2750/14122; C12N 2750/14142; C12N 2750/14141; C12N 2750/14351; C12N 2800/50; C12N 15/8673; C07K 2750/14352; C12N 2750/14152; C07K 14/075
See application file for complete search history.

(56) References Cited

U.S. PATENT DOCUMENTS

| | | | |
|---|---|---|---|
| 5,043,357 A | 8/1991 | Hoffler et al. | |
| 7,776,542 B1* | 8/2010 | Aoyagi ............ | G01N 33/56983 435/5 |
| 2004/0110266 A1 | 6/2004 | Chiorini et al. | |
| 2005/0170519 A1 | 8/2005 | Alam | |
| 2008/0118970 A1 | 5/2008 | Konz et al. | |
| 2008/0132688 A1 | 6/2008 | Zhou | |
| 2009/0275107 A1 | 11/2009 | Lock et al. | |
| 2010/0279385 A1* | 11/2010 | O'Riordan et al. ..... | C12N 7/00 435/239 |
| 2011/0027399 A1 | 2/2011 | Shimamoto et al. | |
| 2016/0152955 A1 | 6/2016 | Sakamoto et al. | |
| 2016/0273058 A1 | 9/2016 | Akashika et al. | |

FOREIGN PATENT DOCUMENTS

| | | |
|---|---|---|
| CN | 102205132 | 10/2011 |
| CN | 102260651 | 11/2011 |
| EP | 0 245 949 | 11/1987 |
| EP | 2 871 239 | 5/2015 |
| JP | 63-14702 | 1/1988 |
| JP | 2001-145496 | 5/2001 |
| JP | 2012-529917 | 11/2012 |
| WO | 97/06272 | 2/1997 |
| WO | 97/08298 | 3/1997 |
| WO | 97/17458 | 5/1997 |
| WO | 00/14205 | 3/2000 |
| WO | 02/12455 | 2/2002 |
| WO | 03/097797 | 11/2003 |

(Continued)

OTHER PUBLICATIONS

Potter M, Lins B, Mietzsch M, Heilbronn R, Van Vliet K, Chipman P, Agbandje-McKenna M, Cleaver BD, Clément N, Byrne BJ, Zolotukhin S. A simplified purification protocol for recombinant adeno-associated virus vectors. Mol Ther Methods Clin Dev. Aug. 13, 2014;1:14034. eCollection 2014.*

Zhou J, Yang X, Wright JF, High KA, Couto L, Qu G. PEG-modulated column chromatography for purification of recombinant adeno-associated virus serotype 9. J Virol Methods. Apr. 2011;173(1):99-107. Epub Feb. 3, 2011.*

Kurogi H, Suzuki T, Akashi H, Ito T, Inaba Y, Matumoto M. Isolation and preliminary characterization of an orbivirus of the Palyam serogroup from biting midge Culicoides oxystoma in Japan. Vet Microbiol. Jan. 1989;19(1):1-11.*

(Continued)

*Primary Examiner* — Rachel B Gill
(74) *Attorney, Agent, or Firm* — Wenderoth, Lind & Ponack, L.L.P.

(57) ABSTRACT

Provided is a method for producing non-enveloped viral particles, comprising a step for obtaining a fraction containing non-enveloped viral particles by removing precipitates which are produced in a step for adding a substance which reduces the solubility of proteins under acidic conditions and/or a substance which precipitates under acidic conditions to a neutral or basic sample containing non-enveloped viral particles, and acidifying the sample after the addition of the substance.

9 Claims, 5 Drawing Sheets

(56) References Cited

FOREIGN PATENT DOCUMENTS

| WO | 2009/123183 | 10/2009 |
|---|---|---|
| WO | 2010/148143 | 12/2010 |
| WO | 2011/074564 | 6/2011 |
| WO | 2013/192604 | 12/2013 |
| WO | 2014/007120 | 1/2014 |
| WO | 2015/005430 | 1/2015 |

OTHER PUBLICATIONS

Marusyk RG, Norrby E. Association of deoxyribonuclease-sensitive material with adenovirus penton aggregates after treatment of infected cell cultures with sodium deoxycholate. Can J Microbiol. Aug. 1971;17(8):1009-13.*

Charney J, Machlowitz R, Tytell AA, Sagin JF, Spicer DS. The concentration and purification of poliomyelitis virus by the use of nucleic acid precipitation. Virology. Nov. 1961;15:269-80.*

Potter M, Lins B, Mietzsch M, Heilbronn R, Van Vliet K, Chipman P, Agbandje-McKenna M, Cleaver BD, Clément N, Byrne BJ, Zolotukhin S. A simplified purification protocol for recombinant adeno-associated virus vectors. Mol Ther Methods Clin Dev. Aug. 13, 2014;1:14034. doi: 10.1038/mtm.2014.34. eCollection 2014.*

Guo P, El-Gohary Y, Prasadan K, Shiota C, Xiao X, Wiersch J, Paredes J, Tulachan S, Gittes GK. Rapid and simplified purification of recombinant adeno-associated virus. J Virol Methods. Aug. 2012;183(2):139-46. Epub Apr. 26, 2012.*

Wang, et al., "Procedures for the efficient purification of pea seed-borne mosaic virus and its genomic RNA", J. Virol. Method., 1992, vol. 36, No. 3, pp. 223-230.

Zhirnov, O. P., "Isolation of Matrix Protein M1 from Influenza Viruses by Acid-Dependent Extraction with Nonionic Detergent", Virology, 1992, vol. 186, No. 1, pp. 324-330.

Guo et al., "Rapid and simplified purification of recombinant adeno-associated virus", J. Virol. Methods, 2012, vol. 183, No. 2, pp. 139-146.

Guo et al., "A simplified purification method for AAV variant by polyethylene glycol aqueous two-phase partitioning", Bioengineered, 2013, vol. 4, No. 2, pp. 103-106.

International Preliminary Report on Patentability dated Jul. 20, 2017 in International Application No. PCT/JP2016/050431.

International Search Report of the International Searching Authority dated Mar. 22, 2016 in International Application No. PCT/JP2016/050431.

Vandenbergh et al., "Efficient Serotype-Dependent Release of Functional Vector into the Culture Medium During Adeno-Associated Virus Manufacturing", Human Gene Therapy, 2010, vol. 21, No. 10, pp. 1251-1257.

Lock et al., Rapid, Simple, and Versatile Manufacturing of Recombinant Adeno-Associated Viral Vectors at Scale:, Human Gene Therapy, 2010, vol. 21, No. 10, pp. 1259-1271.

Zolotukhin et at, "Recombinant adeno-associated virus purification using novel methods improves infectious titer and yield", Gene Therapy, 1999, vol. 6, No. 6, pp. 973-985.

Sokol et al., "Purification of Rabies Virus Grown in Tissue Culture", J. Virol., 1968, vol. 2, No. 8, pp. 836-849.

Gencoglu et al., "Porcine parvovirus flocculation and removal in the presence of osmolytes", J. Biotechnol., 2014, vol. 186, pp. 83-90.

Greenhalgh et al., "Virus Clearance in Your Process from Start to Finish", BioProcessing Journal, 2013, vol. 12, No. 4, pp. 47-52.

R. dos Santos Coura et al., "A role for adeno-associated viral vectors in gene therapy", Genetics and Mol. Biol., 2008, vol. 31, No. 1, pp. 1-11.

R. Morenweiser, "Downstream processing of viral vectors and vaccines", Gene Therapy, 2005, vol. 12, Suppl. 1, pp. S103-S110.

Office Action dated Jan. 25, 2017 in corresponding Chinese patent application No. 201480039156.9, with English translation.

Extended European Search Report dated Feb. 9, 2017 in corresponding European Application No. 14823074.1.

Yokoyama et al., "Removal of small non-enveloped viruses by nanofiltration", Vox Sanguinis, 2004, vol. 86, No. 4, pp. 225-229.

Takimoto et al., "Effect of Hypochlorite-Based Disinfectants on Inactivation of Murine Norovirus and Attempt to Eliminate or Prevent Infection in Mice by Addition to Drinking Water", Exp. Anim., 2013, vol. 62, No. 3, pp. 237-245.

International Preliminary Report on Patentability dated Jan. 12, 2016 in International (PCT) Application No. PCT/JP2014/068438.

International Search Report dated Oct. 14, 2014 in International (PCT) Application No. PCT/JP2014/068438.

U.S. Office Action dated Nov. 7, 2016 in corresponding U.S. Appl. No. 14/900,837.

U.S. Office Action dated Jul. 12, 2017 in corresponding U.S. Appl. No. 14/900,837.

Notification of Reasons for Refusal received Apr. 16, 2019 in corresponding Japanese Application No. 2016-568750, with English translation.

Henderson et al., "Concentration and Purification of Enteroviruses by Membrane Chromatography", Applied and Environmental Microbiology, 1976, vol. 32, No. 5, pp. 689-693.

Office Action dated Dec. 22, 2017 in U.S. Appl. No. 14/900,837.

Taylor, A. C., "Responses of Cells to pH Changes in the Medium", Journal of Cell Biology, 1962, vol. 15, pp. 201-209.

Safaiyan et al., "Selective Effects of Sodium Chlorate Treatment on the Sulfation of Heparan Sulfate", Journal of Biological Chemistry, 1999, vol. 274, No. 51, pp. 36267-36273.

Venkatakrishrtart, B "Endosomal Ph Mediated Structural Transitions in Adeno-Associated Viruses", University of Florida, Doctoral Dissertation, 2012, pp. 1-132.

Office Action dated May 3, 2018 in Chinese Application No. 201480039156.9, with English translation.

Communication pursuant to Article 94(3) EPC issued May 9, 2018 in European Application No. 14823074.1.

Extended European Search Report dated May 30, 2018 in European Application No. 16735082.6.

Henderson et at, "Concentration and Purification of Enteroviruses by Membrane Chromatography", Applied and Environmental Microbiology, 1976, vol. 32, No. 5, pp. 689-693.

Schagen et al., "Ammonium sulphate precipitation of recombinant adenovirus from culture medium: an easy method to increase the total virus yield", Gene Therapy, 2000, vol. 7, No. 18, pp. 1570-1574.

Advisory Action dated Oct. 30, 2017 in U.S. Appl. No. 14/900,837.

Office Action dated Oct. 10, 2017 in corresponding Chinese patent application No. 201480039156.9, with English translation.

* cited by examiner

[Fig. 1]
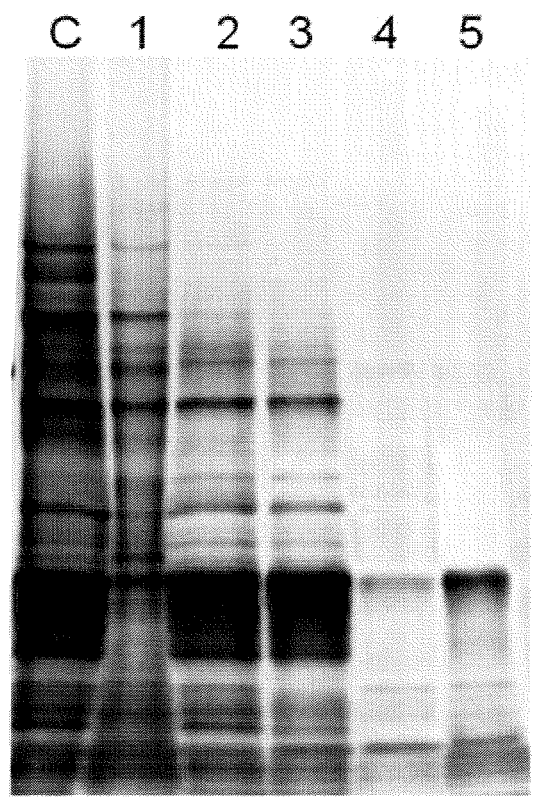

[Fig. 2]
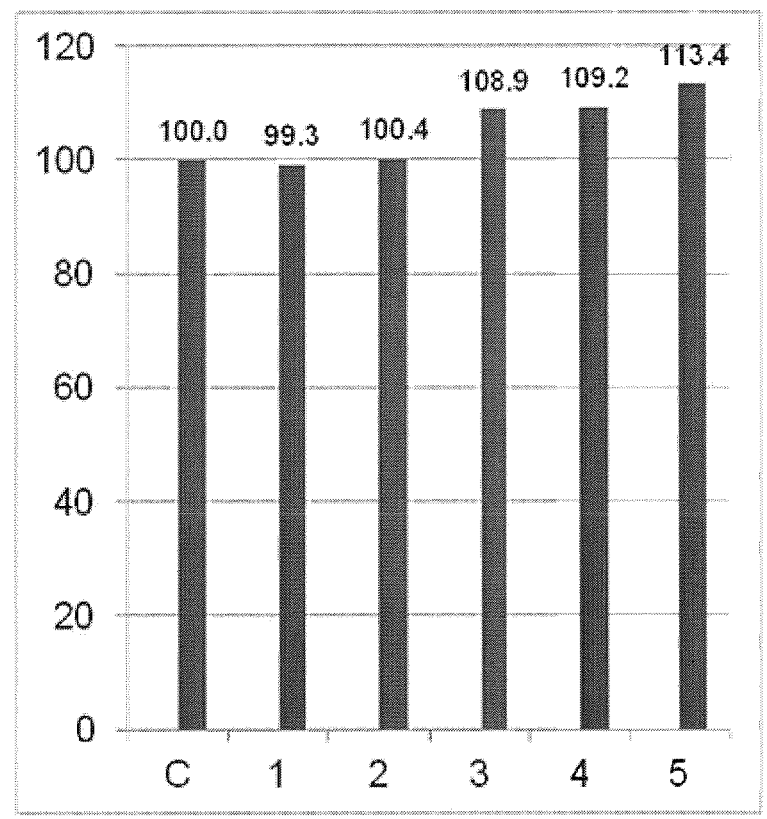

[Fig. 3]
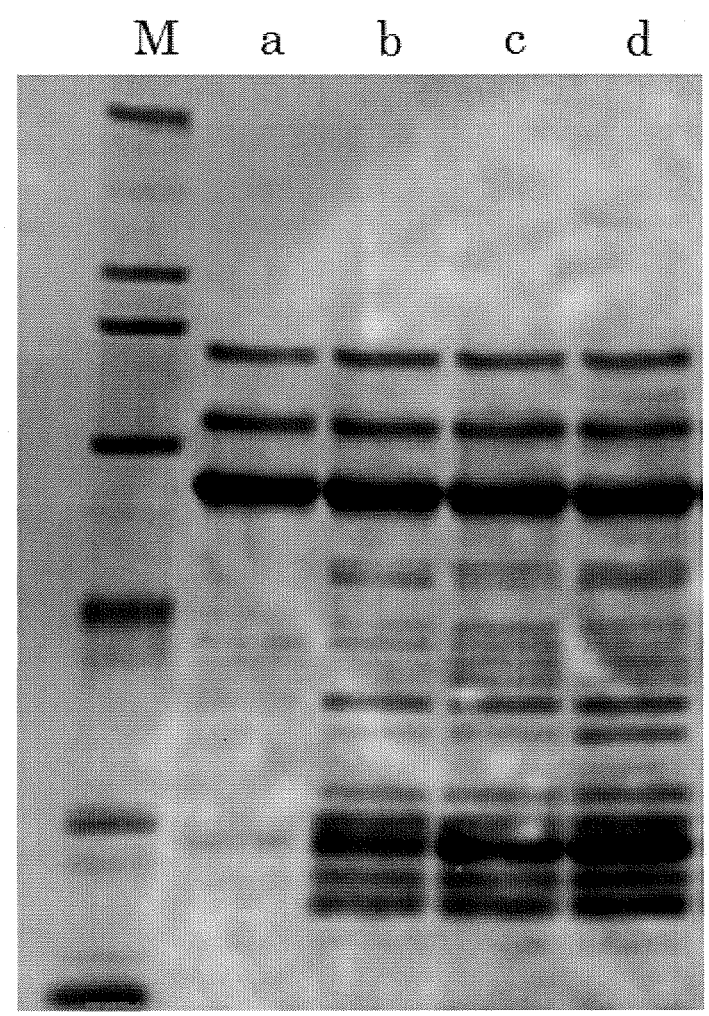

[Fig. 4]
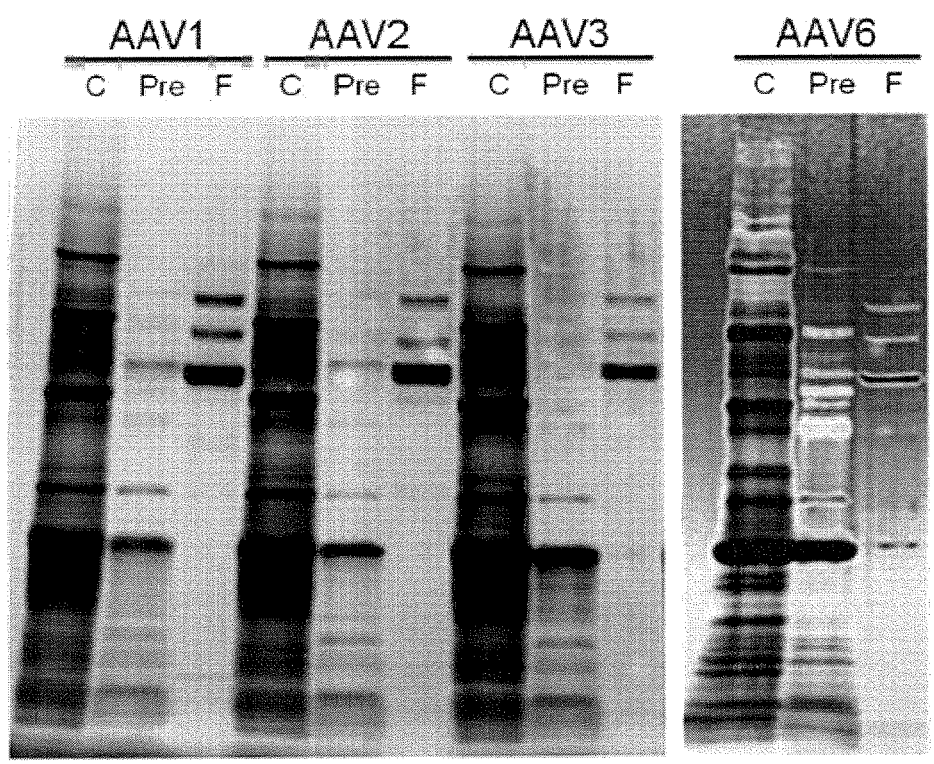

[Fig. 5]
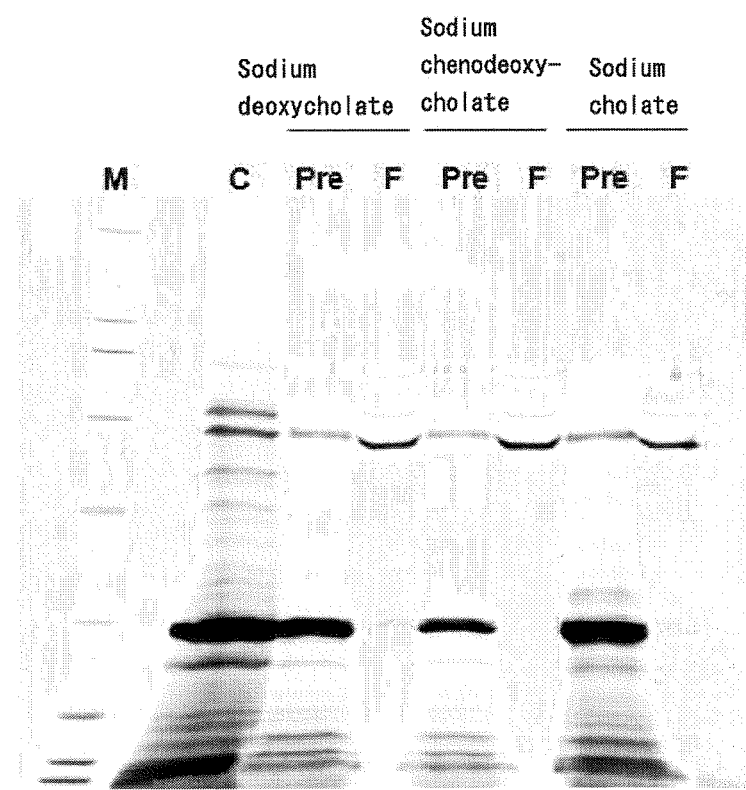

METHOD FOR PRODUCING NON-ENVELOPED VIRAL PARTICLES

TECHNICAL FIELD

The present invention relates to a method of producing a non-enveloped virus particle with high purity and with no laborious operation.

BACKGROUND ART

In the field of gene recombination or the field of medicine, for introduction of a gene into cells of mammals including human, physical methods using electroporation or metal microparticles, chemical methods using nucleic acid, polycation, or liposome, and biological methods using virus-derived vectors for gene transfer (hereinafter, referred to as viral vectors) have been currently used. The viral vectors mean vectors obtained by altering natural viruses so that the viruses can transfer a desired gene or the like into a target, and the development of such vectors has been recently advanced. Viral vectors prepared by gene recombination technology are usually called recombinant viral vectors. Well-known examples of viruses which the recombinant viral vectors are derived from include viruses with envelopes, for example retrovirus, lentivirus, Sendai virus, and herpes virus, and viruses without envelopes (non-enveloped viruses), for example adenovirus, and adeno-associated virus (hereinafter, referred to as AAV).

In particular, AAV can infect a wide variety of cells including human cells, and AAV infects even non-dividing cells in which differentiation terminates, including blood cells, muscle cells, and nerve cells. In addition, since AAV is not pathogenic to human, it has a low risk of adverse effect. The virus particle of AAV is physicochemically stable. For these reasons, AAV has recently attracted attention to utility value as a vector for gene transfer used in gene therapy for the treatment of congenital genetic disease as well as the treatment of cancer or infection.

A method of producing a recombinant viral vector usually comprises introducing elements essential for formation of a virus particle in the form of a nucleic acid construct(s) into a cell to produce a cell having the ability to produce a virus (hereinafter, referred to as a virus-producing cell), and culturing the cell to express the elements essential for formation of the virus particle. In general, of the elements essential for formation of the virus particle, the elements that need to be provided in cis and the elements that can be provided in trans are separately introduced into a cell for viral production, thereby production of a wild-type virus and self-replication of a recombinant virus in a host infected with the virus are prevented (Patent Literature 1).

Hereinafter, as an example, a recombinant vector derived from AAV (hereinafter, referred to as rAAV) is specifically explained. An established method comprises 1) introduction of a rAAV plasmid in which an ITR placed at each end of the wild-type AAV genome is left and rep and cap genes are removed and 2) introduction of a plasmid for expression of rep and cap genes to provide Rep and Cap proteins in trans, and 3) infection with an adenovirus because AAV needs provision of supplemental elements for formation of the infectious virus particle from any virus called a helper virus, such as adenovirus, herpes virus, or vaccinia virus. A vector solution obtained by the above-mentioned method is theoretically contaminated with an adenovirus. In order to avoid the adenovirus contamination, a method of producing a vector comprising, instead of the above-mentioned 3), 3') introduction of a helper plasmid expressing only elements essential for formation of an AAV virus particle among adenovirus-derived elements (Helper-free system) has been developed.

Virus-producing cells that have accomplished viral production are collected and homogenized to obtain a cell homogenate containing rAAV particles. The cell homogenate is subjected to a suitable step such as filtration with a filter, ultracentrifugation, chromatography, or ultrafiltration to purify the rAAV particles as a final product.

At present, as use of viral vectors is extended to the field of basic research or clinical application for gene therapy, a method of obtaining a virus particle with higher titer and higher purity is needed. Various improved methods are disclosed. For example, a method of enhancing production of virus particles and a release rate of the virus particles into a culture supernatant which comprises culturing a virus-producing cell under a stress condition in which a culture medium has an elevated pH is known (Patent Literature 1). Other methods comprise improvement of steps on and after purification of a produced virus. For purification of rAAV particles, a method of purifying rAAV particles of various serotypes without using ultracentrifugation or chromatography is proposed (Non-Patent Literature 1 and Non-Patent Literature 2). However, the said purification method comprises four steps: two-phase separation of a polyethylene glycol (PEG) phase and an aqueous phase, precipitation with PEG, treatment with chloroform, and dialysis; and thus it is complicated. In addition, a product purified by the purification method contains many bands on SDS-PAGE which are probably derived from impurities. Thus, the purification method is not adequate from the viewpoints of purity and simplicity. Therefore, there is still room for improvement in treatment of a virus-producing cell performed before purification of rAAV particles.

CITATION LIST

Patent Literatures

Patent Literature 1: WO 2000/14205

Non-Patent Literatures

Non-Patent Literature 1: J. Virol. Methods, Vol. 183, No. 2, pp. 139-146, 2012
Non-Patent Literature 2: Bioengineered, Vol. 4, No. 2, pp. 103-106, 2013

SUMMARY OF INVENTION

Problems to be Solved by the Invention

An objective of the present invention is to provide a method of producing a non-enveloped virus particle with high purity and with no laborious operation.

Solutions to the Problems

The present inventors intently studied for the purpose of providing a method of producing a non-enveloped virus particle with high purity and with no laborious operation, and as a result, found that a fraction containing a non-enveloped virus particle was obtained by adding a substance which reduces solubility of a protein under an acidic condition and/or a substance which precipitates under an acidic condition to a neutral or basic sample containing a non-enveloped virus particle, and removing a precipitate formed in a step of acidifying the sample after addition of the substance. Thus, the present invention was completed.

The present invention provides:

[1] a method of producing a non-enveloped virus particle, the method comprising:
(a) a step of adding a substance which reduces solubility of a protein under an acidic condition and/or a substance which precipitates under an acidic condition to a neutral or basic sample containing a non-enveloped virus particle,
(b) a step of acidifying the sample to which the substance is added,
(c) a step of removing a precipitate formed in step (b) to obtain a fraction containing the non-enveloped virus particle;

[2] the method according to [1], which further comprises (d) a step of purifying the non-enveloped virus, after step (c);

[3] the method according to [1] or [2], wherein the substance which reduces solubility of a protein under an acidic condition and/or the substance which precipitates under an acidic condition is a surfactant;

[4] the method according to any one of [1] to [3], wherein the step of acidifying is a step of adding an acidic solution;

[5] the method according to any one of [1] to [4], wherein the neutral or basic sample containing a non-enveloped virus particle is a lysate or a homogenate of a non-enveloped virus-producing cell, a culture supernatant of a non-enveloped virus-producing cell which contains a non-enveloped virus particle, or an extract obtained from a non-enveloped virus-producing cell;

[6] the method according to [5], the neutral or basic sample containing a non-enveloped virus particle is a neutralized product of an extract obtained by treating a non-enveloped virus-producing cell with an acidic solution;

[7] the method according to any one of [1] to [6], wherein the neutral or basic sample containing a non-enveloped virus particle is a sample treated with nuclease;

[8] the method according to any one of [1] to [7], wherein the non-enveloped virus particle is adeno-associated virus particle;

[9] a kit for performing the method according to any one of [1] to [8], comprising:
(1) a substance which reduces solubility of a protein under an acidic condition and/or a substance which precipitates under an acidic condition, and
(2) an acidic solution; and

[10] the kit according to [9], which further comprises a neutralizing solution.

Effects of the Invention

According to the present invention, a method of producing a non-enveloped virus particle with high purity and with no laborious operation is provided.

BRIEF DESCRIPTION OF DRAWINGS

FIG. 1 shows results of SDS-PAGE of samples prepared in Example 1.
FIG. 2 shows recovery rates of samples prepared in Example 1.
FIG. 3 shows results of SDS-PAGE of samples prepared in Example 2.
FIG. 4 shows results of SDS-PAGE of samples prepared in Example 3.
FIG. 5 shows results of SDS-PAGE of samples prepared in Example 6.

MODE FOR CARRYING OUT THE INVENTION

The non-enveloped virus as used herein refers to a virus other than an enveloped virus. The enveloped virus refers to a virus having a lipid layer or a lipid bilayer on the viral surface. Representative examples of the non-enveloped virus include DNA genome viruses, for example adenovirus, parvovirus, papovavirus, and human papillomavirus, and RNA genome viruses, for example rotavirus, coxsackie virus, enterovirus, sapovirus, norovirus, poliovirus, echovirus, hepatitis A virus, hepatitis E virus, rhinovirus, and astrovirus.

The non-enveloped virus produced by the production method of the present invention includes, but not limited to, a non-enveloped virus for which a production method has been already known, a non-enveloped virus newly obtained from nature, and gene recombinant viral vectors derived from the above-mentioned non-enveloped viruses. Preferable examples of the non-enveloped virus produced by the production method of the present invention include adenovirus, and AAV belonging to family Parvoviridae. The production method of the present invention is applicable to production of AAV of any known serotype. For example, the production method of the present invention can be used for production of at least one AAV selected from the group consisting of AAV1, AAV2, AAV3, AAV4, AAV5, AAv6, AAV7, AAV8, AAV9, AAV10, AAV11, AAV12, and AAV13. As used herein, the serotype of rAAV is based on the serotype of AAV from which the capsid of the rAAV is derived. In other words, the serotype of rAAV is determined depending on the source of a cap gene used for preparation of the rAAV, and does not depend on the serotype of an AAV genome enclosed in the rAAV particle. For example, when the capsid of rAAV is derived from AAV6 and ITRs in the AAV genome enclosed in the rAAV particle are derived from AAV2, as used herein, the serotype of the rAAV is 6. In addition, the production method of the present invention is applicable to production of AAV comprising variants of AAV capsids of the above-mentioned serotypes.

The "virus particle" as used herein means a particle composed of a protein shell called capsid. The "viral vector" as used herein means a viral genome (the form of nucleic acid) included in the virus particle. For example, in the case of AAV, a rAAV particle is a particle composed of a protein shell called capsid and includes a rAAV vector. The rAAV vector contains a viral genome DNA present in the rAAV particle. The "virus particle" as used herein includes a virus-like particle which does not contain a viral genome (for example, an AAV hollow particle: WO2012/144446). The virus particle includes, but not limited to, a virus-like particle derived from a rAAV vector, and an AAV hollow particle.

As used herein, "acidic" means being at a pH lower than pH 6.5, "neutral" means being at pH 6.5-7.5, and "basic" means being at a pH exceeding pH 7.5.

Hereinafter, the present invention is explained.

(1) Production Method of Non-enveloped Virus Particle of the Present Invention

The production method of a non-enveloped virus particle of the present invention comprises:

(a) a step of adding a substance which reduces solubility of a protein under an acidic condition and/or a substance which precipitates under an acidic condition to a neutral or basic sample containing a non-enveloped virus particle, (b) a step of acidifying the sample to which the substance is added, (c) a step of removing a precipitate formed in step (b) to obtain a fraction containing the non-enveloped virus particle.

Specifically, first, a substance which reduces solubility of a protein under an acidic condition and/or a substance which precipitates under an acidic condition is added to a neutral or basic sample containing a non-enveloped virus particle. Addition of the substance may be performed by addition of a solid substance, or preferably performed by addition of a previously prepared solution at a desired final concentration. The sample may be subjected to next step (b) immediately after addition of the substance, or the sample is preferably left to stand for a while after addition of the substance. The temperature at which the sample is left to stand and the time during which the sample is left to stand may be appropriately determined and are not particularly limited. For example, the temperature at which the sample is left to stand is 0 to 40° C., preferably 4 to 37° C. For example, the time during which the sample is left to stand is 1 minute to 24 hours, preferably 5 minutes to 1 hour. For example, the sample is left to stand at 37° C. for 30 minutes.

The "substance which reduces solubility of a protein under an acidic condition" used in the method of the present invention means a substance having the property of reducing the solubility of a protein under an acidic condition as compared with a neutral or basic condition. The substance is not particularly limited, and is preferably a substance having the property of interacting with a protein in a sample to reduce the solubility of the protein under an acidic condition and allow the protein to precipitate.

The "substance which precipitates under an acidic condition" used in the method of the present invention means a substance having the property of precipitating itself by a change from a neutral or basic condition to an acidic condition. The substance is not particularly limited, and is preferably a substance having the property of precipitating itself together with a protein in a sample under an acidic condition.

The substance which reduces solubility of a protein under an acidic condition and the substance which precipitates under an acidic condition which are used in the method of the present invention may be different substances or may be the same substance. Examples of the substance which reduces solubility of a protein under an acidic condition and/or the substance which precipitates under an acidic condition include, but not limited to, surfactants. The surfactants are roughly classified into anionic surfactants, non-ionic surfactants, cationic surfactants, and amphoteric surfactants.

The anionic surfactants are also called anion surfactants, and ionize in water to become organic anions. The anionic surfactants are classified into carboxylic acid types, sulfonic acid types, sulfate types, and phosphate types. Examples of the carboxylic acid types include deoxycholate salts, cholate salts, and lauroyl sarcosinate salts. Examples of the sulfonic acid types include dodecyl sulfate salts. Preferable examples of the salts include sodium and lithium.

The non-ionic surfactants do not ionize in water. The non-ionic surfactants are classified into ester types, ether types, ester ether types, alkanolamide types, sugar types, and methylglucamine types. Examples of the ester types include polyoxyethylene sorbitan monolaurate [Tween (registered trademark) 20], polyoxyethylene sorbitan monopalmitate [Tween (registered trademark) 40], polyoxyethylene sorbitan monostearate [Tween (registered trademark) 60], and polyoxyethylene sorbitan monooleate [Tween (registered trademark) 80]. Examples of the ether types include polyoxyethylene nonylphenyl ether [Nonidet (registered trademark) P-40], and polyoxyethylene alkyl ether [BriJ (registered trademark) L23, BriJ (registered trademark) L58]. Examples of the ester ether types include polyoxyethylene sorbitan fatty acid ester, polyoxyethylene hexitan fatty acid ester, and sorbitan fatty acid ester polyethylene glycol. Examples of alkanolamide include N,N-bis[3-(D-gluconamido)propyl]deoxycholamide. Examples of the sugar types include alkylmaltoside, and alkylglucopyranoside. Examples of the methylglucamine types include alkyl-N-methylglucamine.

The cationic surfactants are also called cation surfactants, and ionize in water to become organic cations. The cationic surfactants are classified into alkylamine salt types, and quaternary ammonium salt types. Examples of the alkylamine salt types include monomethylamine hydrochloride, dimethylamine hydrochloride, and trimethylamine hydrochloride. Examples of the quaternary ammonium salt types include hexadecyltrimethylammonium bromide and myristyltrimethylammonium bromide.

The amphoteric surfactants mean surfactants having both an anion group and a cation group within the molecule. The amphoteric surfactants ionized in an aqueous solution are similar to amino acids, and the amphoteric surfactants include many amino acid derivatives. Thus, the amphoteric surfactants have an isoelectric point like amino acids. The amphoteric surfactant acts as an anionic surfactant when it is present under more alkaline conditions than the isoelectric point, whereas the amphoteric surfactant acts as a cationic surfactant when it is present under more acidic conditions than the isoelectric point. Examples of the amphoteric surfactants include, but not limited to, sulfobetaine, such as lauryl sulfobetaine, caprylyl sulfobetaine, octyl sulfobetaine, palmityl sulfobetaine, and myristyl sulfobetaine.

In the method of the present invention, an anionic surfactant that insolubilizes at an acidic pH is preferably used. More preferably, a carboxylic acid-type anionic surfactant such as sodium deoxycholate, sodium chenodeoxycholate, sodium cholate, sodium glycocholate, sodium taurocholate, or sodium taurodeoxycholate is used. Especially preferably, sodium deoxycholate, sodium chenodeoxycholate, or sodium cholate is used.

In step (a) of the method of the present invention, the substance which reduces solubility of a protein under an acidic condition and/or the substance which precipitates under an acidic condition may be added as a solid substance, or may be added as a previously prepared solution of the substance. The concentration of the substance in the solution is not particularly limited, and can be appropriately determined by a person skilled in the art. A solvent used for preparing the solution of the substance is not particularly limited, and can be appropriately selected from water, a buffer, a medium for cell culture and the like. The substance which reduces solubility of a protein under an acidic condition and/or the substance which precipitates under an acidic condition is added to the neutral or basic sample containing a non-enveloped virus particle so that the concentration of the substance becomes a desired final concentration. The desired final concentration of the substance is not particularly limited as long as it is such a concentration as allows contaminating proteins in the sample to precipitate under acidic conditions. Although the desired final concentration of the substance depends on the kind of the non-enveloped virus contained in the sample or the kind of the substance, for example, when sodium deoxycholate, sodium chenodeoxycholate, or sodium cholate is used, the final concentration is for example 0.1 to 2% (v/v), preferably 0.2 to 1% (v/v). When the optimum concentration of the substance which reduces solubility of a protein under an acidic condition and/or the substance which precipitates under an acidic condition is varied depending on the kind of the non-enveloped virus, it is natural to determine a suitable concentration of the substance.

Next, in the method of the present invention, the pH of the sample to which the substance is added is acidified. This step may be performed by any method as long as the method can acidify the neutral or basic sample, and the method is not particularly limited. A means for acidifying the sample may be bubbling of a gaseous acid in the sample or addition of solid acid. Especially preferably, a previously prepared acidic solution is added so as to become a desired final concentration. Examples of the acid used in the present invention include compounds selected from the group consisting of citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and their salts, and Good's buffers having a buffering region lower than pH 6.5 such as MES and Bis-Tris. As the acidic solution, for example, a solution containing the above-mentioned compound is used. A solvent for preparing the acidic solution is not particularly limited. The solvent can be appropriately selected from water, a buffer, a medium for cell culture, and the like. Especially preferably, an aqueous solution containing citric acid or a salt thereof is used. The acid or acidic solution is added to the sample so as to become a desired final concentration. The desired final concentration is not particularly limited as long as it is such a concentration as allows the pH of the sample to become acidic. After acidifying the sample, the final pH of the sample is preferably lower than pH 6.5, more preferably in a range of pH 4 to 6. When the optimum pH of the sample is varied depending on the kind of the non-enveloped virus, it is natural to determine a suitable pH of the sample.

The sample containing a non-enveloped virus particle used in the method of the present invention may be a sample derived from a non-enveloped virus-producing cell. The virus-producing cell includes, but not limited to, a virus-producing cell obtained from environment or a clinical sample from a patient with an infection, and an artificially prepared virus-producing cell.

A cell for preparing the non-enveloped virus-producing cell is not particularly limited. Examples of the cell for preparing the non-enveloped virus-producing cell include cells of mammals such as human, monkey, and rodent, and preferable examples thereof include cells having high transformation efficiency, such as a 293 cell (ATCC CRL-1573), a 293T/17 cell (ATCC CRL-11268), a 293F cell, a 293FT cell (all manufactured by Life Technologies Corp.), a G3T-hi cell (WO2006/035829), an Sf9 cell (ATCC CRL-1711), and an AAV293 cell (manufactured by Stratagene Corp.) which is a commercially available cell line for viral production. For example, the 293 cell or the like constantly expresses adenovirus E1 protein. Such a cell modified to transiently or constantly express one or some of proteins necessary for rAAV production may be also used. Into these various cells, a non-enveloped viral vector can be introduced by using a known method or a commercially available kit to obtain non-enveloped virus-producing cells. Culture of the non-enveloped virus-producing cell can be performed under known culture conditions. For example, the cell is cultured at a temperature of 30 to 37° C., a humidity of 95%, and a $CO_2$ concentration of 5 to 10% (v/v). However, culture conditions of the non-enveloped virus-producing cell are not limited to the above-mentioned culture conditions. The cell culture may be performed at a temperature, a humidity and a $CO_2$ concentration out of the above-mentioned ranges, as long as desired cell growth and production of the non-enveloped virus are accomplished. A culture period is not particularly limited, and for example, the cell culture is continued for 12 to 150 hours, preferably 48 to 120 hours Hereinafter, as an example of the non-enveloped virus-producing cell, a rAAV-producing cell is explained. The rAAV-producing cell can be produced by introducing (A) a nucleic acid encoding a Rep protein and a nucleic acid encoding a Cap protein which are derived from AAV, and (B) nucleic acids to provide adenovirus-derived elements, for example, E1a protein, E1b protein, E2 protein, E4 protein, and VA RNA, as elements essential for formation of the rAAV particle, and (C) a nucleic acid to be enclosed in the rAAV particle, into any cell. A method wherein an adenovirus or the like is used as a helper virus instead of the nucleic acids described in the above (B) is also known.

The nucleic acid encoding a Rep protein and the nucleic acid encoding a Cap protein which are derived from AAV, and the nucleic acids to provide adenovirus-derived elements may be in any form which is not limited. These nucleic acids can be inserted into a plasmid or a viral vector as one or more nucleic acid constructs capable of providing the elements, and then the plasmid or the viral vector can be introduced into a cell. The introduction of these nucleic acids into a cell can be performed by a known method using a commercially available or known plasmid or viral vector.

The nucleic acid to be enclosed in the rAAV particle is composed of ITR sequences derived from AAV and a nucleic acid desired to be carried by a rAAV vector. Examples of the nucleic acid desired to be carried by a rAAV vector include any foreign gene, for example a nucleic acid for providing a polypeptide (enzyme, growth factor, cytokine, receptor, structural protein, etc.), an antisense RNA, a ribozyme, a decoy, an RNA that induces RNA interference, or the like. In addition, for control of expression of the foreign gene, a suitable promoter, enhancer, terminator and other transcriptional regulatory elements may be inserted into the nucleic acid. For example, the nucleic acid to be enclosed in the rAAV particle may contain any foreign gene desired to be carried by the rAAV vector between two ITR sequences, or may contain any foreign gene desired to be carried by the rAAV vector and at least one element for control of expression of the foreign gene between two ITR sequences. The nucleic acid to be enclosed in the virus particle can be introduced as a nucleic acid construct in the form of a plasmid into a cell. The plasmid can be constructed, for example, by use of a pAAV-CMV vector (manufactured by TAKARA BIO Inc.) which is commercially available, or the like.

The neutral or basic sample containing a non-enveloped virus particle used in the method of the present invention can be prepared by, for example, destruction or lysis of the non-enveloped virus-producing cell cultured as described above. In the case where non-enveloped virus particles leak into a medium during culture of the non-enveloped virus-producing cell, a culture supernatant containing the non-enveloped virus particles may be used as the sample. The destruction or lysis of the non-enveloped virus-producing cell can be performed by a known method such as ultrasonic treatment, freeze-thaw treatment, enzymatic treatment, or osmotic pressure treatment. When a lysate or homogenate of the non-enveloped virus-producing cell thus obtained or the culture supernatant containing the non-enveloped virus particles has a neutral or basic pH, the lysate or homogenate or the culture supernatant can be directly used as the neutral or basic sample containing a non-enveloped virus particle. When the lysate or homogenate or the culture supernatant does not a neutral or basic pH, the lysate or homogenate or the culture supernatant can be neutralized to obtain the neutral or basic sample containing a non-enveloped virus particle to be used in the method of the present invention. As used herein, neutralization means, but not limited to, adding a basic solution or a pH buffer to an acidic solution. A solution after neutralization (neutralized product) may be neutral or basic. Examples of the basic solution include, but not limited to, a sodium hydroxide solution and a potassium hydroxide solution. Examples of the PH buffer include, but not limited to, a Tris-HCl solution.

The neutral or basic sample containing a non-enveloped virus particle to be used in the method of the present invention may be also a neutralized product of an extract obtained by treating the non-enveloped virus-producing cell with an acidic solution. Specifically, the sample, which is obtained by bringing the non-enveloped virus-producing cell into contact with an acidic solution and then is neutralized can be preferably used. This step is performed by suspending a pellet of the non-enveloped virus-producing cell in an acidic solution, wherein the pellet is collected by removing a culture solution by centrifugation or filtration after the cell culture, or by adding a component to the culture solution of the non-enveloped virus-producing cell, wherein the component is a component capable of making a culture solution acidic. The acidic solution is not limited, as long as the acidic solution shows a lower pH than that of the non-enveloped virus-producing cell being cultured and the acidic solution enables preparation of an extract containing non-enveloped virus particles from the non-enveloped virus-producing cell that has accomplished the viral production. Examples of the acidic solution include the same solutions as examples of the acidic solution used in step (b) of the method of the present invention. The component capable of making a culture solution acidic is not limited, as long as the component changes the pH of the culture solution of the non-enveloped virus-producing cell into a lower pH than that of the non-enveloped virus-producing cell being cultured and the component enables preparation of an extract containing non-enveloped virus particles from the non-enveloped virus-producing cell that has accomplished the viral production. Examples of the component include the same compounds as examples of the acid used in step (b) of the method of the present invention. Examples of temperature and time for the contact with the acidic solution or the component capable of making a culture solution acidic include, but not particularly limited to, 0 to 40° C., preferably 4 to 37° C., and 1 minute to 48 hours, preferably 5 minutes to 24 hours. The non-enveloped virus-producing cell in a state of contact with the acidic solution or the component capable of making a culture solution acidic, or the extract in a state after neutralization can be also stored in an ultra-deep freezer, for example at −80° C., for a long time. This contact step results in the release of non-enveloped virus outside the virus-producing cell.

The neutral or basic sample containing a non-enveloped virus particle used in the method of the present invention may be previously treated with nuclease. For example, before addition of the substance which reduces solubility of a protein under an acidic condition and/or the substance which precipitates under an acidic condition, the sample containing a non-enveloped virus particle may be treated with nuclease. The nuclease used in this step is preferably a nuclease that acts on DNA contained in the extract. Examples of the nuclease include BENZONASE (registered trademark) (manufactured by Merck Millipore Corporation), and Cryonase Cold-active nuclease (manufactured by TAKARA BIO INC.). Temperature and time for the nuclease treatment is not particularly limited, and may be appropriately determined depending on the kind of the nuclease to be used.

In the method of the present invention, the step of removing the formed precipitate to obtain a fraction containing the non-enveloped virus particle means a step of removing the precipitate formed in the step of acidifying to obtain a fraction containing the non-enveloped virus particle. The precipitate may be removed by a known solid-liquid separation method such as filtration, preferably centrifugation.

The fraction containing the non-enveloped virus particle obtained via the step of removing the precipitate may be further subjected to a purification step. By the purification step, the non-enveloped virus particle may be concentrated. Examples of a method for the purification include ultracentrifugation, chromatography, ultrafiltration, and other known methods.

The ultrafiltration means filtration using an ultrafiltration membrane. The ultrafiltration membrane means a separation membrane having physically definite many fine pores. The molecular weight cut off of the ultrafiltration membrane is preferably 50 to 300 kDa, more preferably 70 to 150 kDa, further preferably 100 kDa in terms of purification of non-enveloped virus and removal of contaminating substances. For example, ultrafiltration membrane Amicon (registered trademark) Ultra-15 having a molecular weight cut off of 100 kDa (manufactured by Merck Millipore Corporation; hereinafter referred to as a 100 kDa ultrafiltration membrane) can be used. At the same time, polyethylene glycol (PEG) can be added to the fraction containing the non-enveloped virus particle to improve a recovery rate of the non-enveloped virus particle. The PEG to be added is not particularly limited, and PEG having various average molecular weights can be used. For example, PEG having an average molecular weight of 200 to 10,000, preferably an average molecular weight of 4,000 to 8,000 is used in the present invention. More preferably, PEG having an average molecular weight of 6,000 can be used.

The purification of the non-enveloped virus particle by chromatography can be performed by an ion-exchange column (for example, Mustang Q manufactured by Pall Corp.), an affinity column (for example, AVB Sepharose (registered trademark) manufactured by GE Healthcare Ltd., or a heparin column), a hydroxyapatite column, or the like.

In the method of the present invention, the non-enveloped virus particle is preferably adeno-associated virus particle.

In the method of the present invention, the yield of the non-enveloped virus particle is shown as the titer of the non-enveloped virus or the like. The titer of the non-enveloped virus is shown as, but not limited to, in a certain amount of a sample, (a) the number of genomes (genomic titer) of the non-enveloped virus, (b) the infection ability (infectious titer) of the non-enveloped virus to a cell as determined experimentally, or (c) the purity of protein constituting the non-enveloped virus as measured.

Examples of a method for determining the above (a) include a method comprising determination the copy number of the virus genome in a sample by PCR. For the determination of genomic titer, for example, AAVpro (registered trademark) Titration Kit (for Real Time PCR) Ver. 2 (manufactured by TAKARA BIO INC.) is used, and the genomic titer can be calculated by a method as described in the attached instruction manual.

Examples of a method for determination of the above (b) include a method comprising infection of a suitable target cell with serially diluted solutions of the non-enveloped virus, and detection of change in the form of the cell (cytopathy), a method comprising detection of the expression of a transgene, and a method comprising determination of the copy number of the virus genome introduced into the cell.

Examples of a method for determination of the above (c) include a method comprising SDS-PAGE analysis of the protein and a method comprising quantitative determination of the protein by an immunological technique.

(2) Kit for Production Method of the Present Invention

The kit of the present invention is a kit for performing the method of producing a non-enveloped virus particle as described in the above section (1), and contains (1) a substance which reduces solubility of a protein under an acidic condition and/or a substance which precipitates under an acidic condition and (2) an acidic solution. As the substance which precipitates under an acidic condition, the substance which reduces solubility of a protein under an acidic condition and/or the substance which precipitates under an acidic condition as explained in the above section (1) "production method of non-enveloped virus particle of the present invention" can be preferably used. The acidic solution is not particularly limited as long as it can be used in the step of acidifying the pH of the sample to which the substance which reduces solubility of a protein under an acidic condition and/or the substance which precipitates under an acidic condition is added as explained in the above section (1) "production method of non-enveloped virus particle of the present invention". The kit of the present invention may further comprise a neutralizing solution. The neutralizing solution is preferably a basic solution or a pH buffer. Examples of the basic solution include, but not limited to, a sodium hydroxide solution and a potassium hydroxide solution. Examples of the pH buffer include, but not limited to, a Tris-HCl solution. The kit may further contain a reagent to be used for preparation of the extract from the non-enveloped virus-producing cell, a plasmid comprising a nucleic acid to provide elements essential for particle formation of the non-enveloped virus, a plasmid comprising a nucleic acid to be enclosed in the particle of the non-enveloped virus, or the like.

According to the present invention, in addition to the method of producing a non-enveloped virus particle, the kit for use in the production method, and the non-enveloped virus particle produced by the production method are provided. The non-enveloped virus particle obtained by using the production method of the present invention can be used as an active ingredient for pharmaceutical compositions. The pharmaceutical compositions can be used ex vivo for cells from patients, or administered directly to patients.

EXAMPLES

Hereinafter, the present invention is more specifically explained by way of Examples which the present invention is not limited to.

Example 1: Purification of rAAV5 by Addition of Sodium Deoxycholate and Addition of Citric Acid (1) Seeding of Cell for Production of rAAV In DMEM (manufactured by Sigma-Aldrich Co. LLC.) containing 10% FBS (manufactured by Gibco), 293T/17 cells were suspended. The suspension was seeded in a tissue culture treated T225 flask (manufactured by Corning Inc.), and then, cultured in a $CO_2$ incubator of 5% (v/v) $CO_2$ at 37° C. for 2 days.

(2) Transfection of Plasmid for Production of rAAV5

The cells obtained by Example 1-(1) were transfected with each 25 µg of a pRC5 vector containing sequences encoding AAV2 Rep protein and AAV5 Cap protein (manufactured by TAKARA BIO INC.), a pHelper vector containing sequences encoding adenovirus-derived E2A, VA and V4 (manufactured by TAKARA BIO INC.), and a pAAV-ZsGreen1 vector containing an expression cassette for fluorescent protein ZsGreen1 between two ITRs of AAV2 genome (manufactured by TAKARA BIO INC.) by using a calcium phosphate method. Six hours after the transfection, the medium was completely removed, and 40 mL/flask of DMEM containing 2% fetal bovine serum (FBS) was added to the flask. The cells were cultured in a $CO_2$ incubator of 5% (v/v) $CO_2$ at 37° C. for 2 days.

(3) Preparation of Extract by Citrate Buffer Treatment

To the flask obtained by Example 1-(2), 0.5 mL of 0.5 M EDTA (manufactured by Wako Pure Chemical Industries, Ltd.) was added. The flask was left to stand at room temperature for several minutes to dissociate the cells. Then, the culture solution containing the cells was collected, centrifuged at 1,750×g for 10 minutes at 4° C. Then, a supernatant was removed. A cell pellet was resuspended in 2 mL of a citrate buffer (38.1 mM citric acid, 74.8 mM sodium citrate, 75 mM sodium chloride, 100 mM magnesium chloride, pH 5), mixed for 15 seconds by a vortex mixer, left to stand at room temperature for 5 minutes, again mixed by a vortex mixer for 15 seconds, and then centrifuged at 14,000×g for 10 minutes at 4° C. to collect a supernatant. To the supernatant, 1/10 volume of 2 M Tris-HCl (pH 9.5) was added, and the solution thus obtained was used as an extract.

(4) Formation and Removal of Precipitate by Addition of Sodium Deoxycholate and Addition of Citric Acid To the extract obtained by Example 1-(3), 1/100 volume of 20 U/µL Cryonase (registered trademark) Cold-active Nuclease (manufactured by TAKARA BIO INC.) was added (final concentration: 0.2 U/µL), and then reacted at 37° C. for 1 hour. The reaction sample was divided into 5 aliquots. To sample 1, 1/10 volume of 1 M citric acid was only added. To sample 2, 1/10 volume of 5% (v/v) sodium deoxycholate was only added. To sample 3, 1/10 volume of 5% (v/v) sodium deoxycholate was added, and after the sample was left to stand at 37° C. for 30 minutes, 1/40 volume of 1 M citric acid was further added. To sample 4, 1/10 volume of 5% (v/v) sodium deoxycholate was added, and after the sample was left to stand at 37° C. for 30 minutes, 1/20 volume of 1 M citric acid was further added. To sample 5, 1/10 volume of 5% (v/v) sodium deoxycholate was added, and after the sample was left to stand at 37° C. for 30 minutes, 1/10 volume of 1 M citric acid was further added. Each sample was subjected to pH measurement. Results are shown in Table 1.

TABLE 1

| Sample | 5% (v/v) sodium deoxycholate | 1M citric acid | pH |
|---|---|---|---|
| 1 | No addition | 1/10 volume (final concentration 0.1M) | 3 |
| 2 | 1/10 volume (final concentration 0.5% (v/v)) | No addition | 8 |
| 3 | 1/10 volume (final concentration 0.5% (v/v)) | 1/40 volume (final concentration 0.025M) | 7 |
| 4 | 1/10 volume (final concentration 0.5% (v/v)) | 1/20 volume (final concentration 0.05M) | 6 |
| 5 | 1/10 volume (final concentration 0.5% (v/v)) | 1/10 volume (final concentration 0.1M) | 4 |

In all the samples, a precipitate was formed. The sample was centrifuged at 5,000×g for 5 minute at 4° C., and a supernatant was collected to remove the precipitate. The collected supernatant was filtered with pressure-driven filter unit Millex (registered trademark) made of PVDF having a pore size of 0.45 μm (manufactured by Merck Millipore Corp.; hereinafter, referred to as a 0.45 μm pore size filter) to obtain a filtrate as rAAV5 before concentration (samples 1-5).

(5) Determination of Purity of rAAV5 Before Concentration

Each of the extract obtained by Example 1-(3) and the 5 types of rAAV5 before concentration obtained by Example 1-(4) was mixed with an equal amount of 5× sample buffer (manufactured by TAKARA BIO Inc.) and kept at 95° C. for 10 minutes. Each mixture (4 μL) was applied onto a 4-12% polyacrylamide gel and electrophoresed. After completion of electrophoresis, the gel was immersed in a suitable amount of an Oriole fluorescent gel stain solution (manufactured by Bio-Rad Laboratories, Inc.), and shaken under light shielding for 90 minutes. After shaking, the gel was photographed with Luminoshot 400 (manufactured by TAKARA BIO Inc.). Results are shown in FIG. 1. In FIG. 1, lane C shows the extract, and lanes 1-5 show the rAAV5 before concentration (samples 1-5).

All bands found in FIG. 1 are bands corresponding to contaminating proteins. Since the concentration of rAAV5 at a stage before concentration is low, bands corresponding to rAAV5 are not detected. As seen in FIG. 1, the numbers of bands corresponding to contaminating proteins found in lane 1 and lane 2 were low as compared with lane C. These results show that contaminating proteins can be precipitated and removed by addition of citric acid or addition of sodium deoxycholate to a mixture of rAAV5 and the contaminating proteins. As seen in FIG. 1, the numbers of bands corresponding to contaminating proteins found in lanes 3-5 were low as compared with lanes 1 and 2. These results show that the contaminating proteins can be more efficiently precipitated and removed by a combination of addition of sodium deoxycholate and addition of citric acid. In addition, it was found that the removal efficiency of contaminating proteins was varied depending on the addition amounts of sodium deoxycholate and citric acid. Specifically, the numbers of bands corresponding to contaminating proteins found in lane 4 and lane 5 were very low. Thus, the contaminating proteins were efficiently removed when sodium deoxycholate was added at a final concentration of 0.5% (v/v) and citric acid was added so as to become pH 4 to 6.

(6) Determination of Recovery Rate of rAAV5 Before Concentration

The genomic titers of the extract obtained by Example 1-(3) and the 5 types of rAAV5 before concentration obtained by Example 1-(4) were determined. For determination of the genomic titer, AAVpro (registered trademark) Titration Kit (for Real Time PCR) Ver. 2 (manufactured by TAKARA BIO INC.) was used, and operations including preparation of a reaction solution etc. followed the instructions attached to the kit. Based on data of genomic titers thus obtained, a total genomic titer was calculated by the following formula.

Formula: Total genomic titer $(VG)$=genomic titer $(VG/mL)$× total fluid volume (mL)

Assuming that the total genomic titer of the extract is 100, a value relative to the total genomic titer of the extract (a recovery rate) is shown in FIG. 2. In FIG. 2, the vertical axis shows a recovery rate (%), and on the horizontal axis, lane C shows the extract, and lanes 1-5 show the rAAV5 before concentration (samples 1-5).

As seen in FIG. 2, the recovery rates of samples 1-5 were 99% to 113%, which were near 100%. These results show that when rAAV5 is purified by addition of sodium deoxycholate and addition of citric acid, the recovery rate of rAAV5 is very high.

The results of FIG. 1 and FIG. 2 show that the purification of rAAV5 by addition of sodium deoxycholate and addition of citric acid is a very efficient purification method. Specifically, contaminating proteins can be precipitated and removed by addition of sodium deoxycholate and addition of citric acid. It was particularly found that rAAV5 was purified at a high recovery rate when sodium deoxycholate was added at a final concentration of 0.5% (v/v) and citric acid was added so as to become pH 4 to 6.

Example 2: Purification and Concentration of rAAV5

(1) Study of Addition Amount of Sodium Deoxycholate and Citric Acid

An extract was prepared in the same manner as Example 1-(1) to (3). To the extract, 1/100 volume of 20 U/μL Cryonase (registered trademark) Cold-active Nuclease (manufactured by TAKARA BIO INC.) was added (final concentration: 0.2 U/μL), and then reacted at 37° C. for 1 hour. The reaction sample was divided into 4 aliquots. To the samples, 1/10 volume or 1/20 volume of 5% (v/v) sodium deoxycholate was added, and after the sample was left to stand at 37° C. for 30 minutes, 1/20 volume or 1/30 volume of 1 M citric acid was further added. Each sample was subjected to pH measurement. Results are shown in Table 2.

TABLE 2

| Sample | 5% (v/v) sodium deoxycholate | 1M citric acid | pH |
|---|---|---|---|
| a | 1/10 volume (final concentration 0.5% (v/v)) | 1/20 volume (final concentration 0.05M) | 5 |
| b | 1/10 volume (final concentration 0.5% (v/v)) | 1/30 volume (final concentration 0.033M) | 6 |
| c | 1/20 volume (final concentration 0.25% (v/v)) | 1/20 volume (final concentration 0.05M) | 5 |

TABLE 2-continued

| Sample | 5% (v/v) sodium deoxycholate | 1M citric acid | pH |
|---|---|---|---|
| d | 1/20 volume (final concentration 0.25% (v/v)) | 1/30 volume (final concentration 0.033M) | 5 |

In all the samples, a precipitate was formed. The sample was centrifuged at 5,000×g for 5 minute at 4° C., and a supernatant was collected to remove the precipitate. The collected supernatant was filtered with a 0.45 μm pore size filter to obtain a filtrate as rAAV5 before concentration.

(2) Purification and Concentration of rAAV5 by Ultrafiltration Membrane

The rAAV5 before concentration obtained by Example 2-(2) was put on a 100 kDaK ultrafiltration membrane (manufactured by Merck Millipore Corp.), and centrifuged at 2,000×g for 10 minutes at 4° C. A filtrate was discarded. Further, "a series of operations (washing operation) wherein 10 mL of D-PBS was added onto the ultrafiltration membrane, suspended and centrifuged under the above-mentioned conditions, and a filtrate was discarded" was repeated 5 times to obtain a final concentrate as purified rAAV5 (samples a-d). By this series of operations, contaminating substances having low molecular weight were removed and rAAV5 was 10-fold concentrated.

(3) Determination of Purity of rAAV5

The purity of the purified rAAV5 obtained by Example 2-(2) was determined in the same manner as Example 1-(5). Results are shown in FIG. 3. In FIG. 3, lane M shows Protein Molecular Weight Marker (Broad) (manufactured by TAKARA BIO INC.; 200, 116, 97, 66, 44, 29, 20 kDa from the top), and lanes a-d show the purified rAAV5 (samples a-d).

In FIG. 3, 3 bold bands are bands corresponding to structural proteins (VP1, VP2, VP3) of rAAV5, and other bands are bands corresponding to contaminating proteins. As seen from FIG. 3, lane a had a low number of bands corresponding to contaminating proteins. This result shows that rAAV5 can be purified and concentrated by removing a precipitate formed by addition of sodium deoxycholate (final concentration 0.5% (v/v)) and addition of citric acid (pH 5), and then performing the treatment with a 100 kDaK ultrafiltration membrane.

Example 3: Purification of rAAV of Various Serotypes (rAAV1, rAAV2, rAAV3, rAAV6)

(1) Seeding of Cell for Production of rAAV

Cells for production of rAAV were seeded in the same manner as Example 1-(1).

(2) Transfection of Plasmid for Production of rAAV

The cells obtained by Example 3-(1) were transfected with a plasmid for production of rAAV in the same manner as Example 1-(2), except that a pRep-Cap1 AAV helper plasmid (manufactured by Applied Viromics), a pRC2-mi342 vector (manufactured by TAKARA BIO INC.), a pRep-Cap3 AAV helper plasmid (manufactured by Applied Viromics), or a pRC6 vector (manufactured by TAKARA BIC INC.) was used instead of the pRC5 vector according to the serotype of rAAV to be prepared.

(3) Preparation of Extract by Citrate Buffer Treatment

An extract of rAAV of each serotype was prepared in the same manner as Example 1-(3).

(4) Formation and Removal of Precipitate by Addition of Sodium Deoxycholate and Addition of Citric Acid To the extract obtained by Example 3-(3), 1/100 volume of 20 U/μL Cryonase (registered trademark) Cold-active Nuclease (manufactured by TAKARA BIO INC.) was added (final concentration: 0.2 U/μL), and then reacted at 37° C. for 1 hour. Then, 1/10 volume of 5% (v/v) sodium deoxycholate was added to each sample. After the sample was left to stand at 37° C. for 30 minutes, 1/20 volume of 1 M citric acid was further added to each sample. Each sample was subjected to pH measurement. As a result, each sample had pH 4 to 6.

In all the samples, a precipitate was formed. The sample was centrifuged at 5,000×g for 5 minute at 4° C., and a supernatant was collected to remove the precipitate. The collected supernatant was filtered with a 0.45 μm pore size filter to obtain a filtrate as rAAV before concentration.

(5) Purification and Concentration of rAAV by Ultrafiltration Membrane

The rAAV before concentration obtained by Example 3-(4) was put on a 100 kDaK ultrafiltration membrane, and centrifuged at 2,000×g for 5 minutes or more at 4° C. A filtrate was discarded. Further, "a series of operations (washing operation) wherein 14 mL of D-PBS was added onto the ultrafiltration membrane, suspended and centrifuged under the above-mentioned conditions, and a filtrate was discarded" was repeated 5 times to obtain a final concentrate as purified rAAV. By this series of operations, contaminating substances having low molecular weight were removed and rAAV was 3 to 5-fold concentrated.

(6) Determination of Purity of rAAV

The purity of the extract (lane C), the rAAV before concentration (lane Pre), and the purified rAAV (lane F) of rAAV of each serotype was determined in the same manner as Example 1-(5). Results are shown in FIG. 4.

In FIG. 4, all bands found in lane C and lane Pre are bands corresponding to contaminating proteins. Since the concentration of rAAV at this stage is low, bands corresponding to rAAV are not detected. In contrast, 3 bold bands found in lane F are bands corresponding to structural proteins (VP1, VP2, VP3) of rAAV. As seen from FIG. 4, regarding rAAV of each serotype, lane Pre had a low number of bands corresponding to contaminating proteins as compared with lane C. This result shows that the contaminating proteins can be precipitated and removed by addition of sodium deoxycholate and addition of citric acid regardless of the serotype of rAAV. In addition, regarding rAAV of each serotype, lane F had few bands corresponding to contaminating proteins other than the bands corresponding to structural proteins (VP1, VP2, VP3) of rAAV. This result shows that rAAV can be concentrated and contaminating proteins having low molecular weight can be removed by the treatment with a 100 kDaK ultrafiltration membrane regardless of the serotype of rAAV.

(7) Determination Recovery Rate of rAAV

The genomic titer of rAAV of each serotype was determined in the same manner as Example 1-(6). The total genomic titer of rAAV at each step was calculated. Assuming that the total genomic titer of the extract is 100, a value relative to the total genomic titer of the extract (a recovery rate) is shown in Table 3.

TABLE 3

| rAAV serotype | Step | |
| --- | --- | --- |
| | Extract (C) | Before concentration (Pre) |
| rAAV1 | 100% | 115.6% |
| rAAV2 | | 89.9% |
| rAAV3 | | 105.9% |
| rAAV6 | | 120.5% |

As seen in Table 3, the recovery rates of rAAV before concentration (Pre) were 89% to 120%, which were near 100%. These results show that when rAAV is purified by addition of sodium deoxycholate and addition of citric acid, the recovery rate of rAAV is very high regardless of the serotype of rAAV.

The results of FIG. 4 and Table 3 show that the purification of rAAV by addition of sodium deoxycholate and addition of citric acid is a very efficient purification method regardless of the serotype of rAAV. Specifically, contaminating proteins can be precipitated and removed by adding sodium deoxycholate at a final concentration of 0.5% (v/v) and adding citric acid so as to become pH 4 to 6. Further, it was found that rAAV was obtained with higher purity by additionally performing the treatment with a 100 kDaK ultrafiltration membrane.

Example 4: Improvement of Recovery Rate of rAAV6 by Addition of Polyethylene Glycol (1) Preparation of rAAV6 Before Concentration In the same manner as Example 3-(1) to (4), rAAV6 before concentration was prepared.

(2) Purification and Concentration of rAAV6 by Ultrafiltration Membrane (Addition of Polyethylene Glycol)

The rAAV6 before concentration was divided into 3 aliquots. To sample 1, polyethylene glycol was not added. To sample 2, a solution of polyethylene glycol (PEG)-6000 (manufactured by Sigma-Aldrich Co. LLC.) was added to become a final concentration of 0.4% (w/v). To sample 3, PEG-600 was added to become a final concentration of 0.8% (w/v). Each sample was put on a 100 kDaK ultrafiltration membrane, and centrifuged at 2,380×g for 10 minutes or more at room temperature. A filtrate was discarded. Further, "a series of operations (washing operation) wherein 10 to 14 mL of PBS containing polyethylene glycol at each final concentration was added onto the ultrafiltration membrane, suspended and centrifuged under the above-mentioned conditions, and a filtrate was discarded" was repeated 3 times. Only sample 2 and sample 3 were additionally washed with PBS. A final concentrate was obtained as purified rAAV6. By this series of operations, contaminating substances having low molecular weight were removed and rAAV6 was 6 to 12-fold concentrated.

(3) Determination Recovery Rate of rAAV6

The genomic titer of each rAAV6 was determined in the same manner as Example 1-(6). The total genomic titer of each rAAV6 at each step was calculated. Assuming that the total genomic titer of the extract is 100, a value relative to the total genomic titer of the extract (a recovery rate) is shown in Table 4.

TABLE 4

| | | Step | | |
| --- | --- | --- | --- | --- |
| Sample | Polyethylene glycol | Extract (C) | Before concentration (Pre) | Purified (F) |
| 1 | No addition | 100% | 107.9% | 30.8% |
| 2 | 0.4% (w/v) | | | 41.4% |
| 3 | 0.8% (w/v) | | | 65.2% |

As seen in Table 4, the recovery rate of rAAV6 was improved by addition of polyethylene glycol upon the purification and concentration of rAAV6 using an ultrafiltration membrane. It is believed that the recovery rate of rAAV of other serotypes can be also improved by addition of polyethylene glycol upon ultrafiltration.

Example 5: Study of Various Kinds of Acidic Solutions (1) Preparation of Extract of rAAV6

An extract of rAAV6 was prepared in the same manner as Example 3-(1) to (3).

(2) Formation and Removal of Precipitate by Addition of Sodium Deoxycholate and Addition of Various Kinds of Acidic Solutions To the rAAV6 extract obtained by Example 5-(1), 1/100 volume of 20 U/μL Cryonase (registered trademark) Cold-active Nuclease was added (final concentration: 0.2 U/μL), and then reacted at 37° C. for 1 hour. A part of the reaction sample was divided into 3 aliquots. To each sample, 1/10 volume of 5% (v/v) sodium deoxycholate was added, and after the sample was left to stand at 37° C. for 30 minutes, 1/20 volume of 1 M citric acid, 1/20 volume of 1 M hydrochloric acid, or 1/20 volume of 1 M acetic acid was added. Each sample was confirmed to be acidic by pH measurement. The conditions of each sample are shown in Table 5.

TABLE 5

| Sample | 5% (v/v) sodium deoxycholate | Acidic solution |
| --- | --- | --- |
| 1 | 1/10 volume (final concentration 0.5% (v/v)) | 1M citric acid, 1/20 volume (final concentration 0.05M) |
| 2 | 1/10 volume (final concentration 0.5% (v/v)) | 1M hydrochloric acid, 1/20 volume (final concentration 0.05M) |
| 3 | 1/10 volume (final concentration 0.5% (v/v)) | 1M acetic acid, 1/20 volume (final concentration 0.05M) |

In all the samples, a precipitate was formed. The sample was centrifuged at 5,000×g for 5 minute at 4° C., and a supernatant was collected to remove the precipitate. The collected supernatant was filtered with a 0.45 μm pore size filter to obtain a filtrate as rAAV6 before concentration.

(3) Determination of Purity and Recover Rate of rAAV6 Before Concentration

The purity of rAAV6 before concentration was determined in the same manner as Example 1-(5). As a result, the rAAV6 before concentration had equal purity regardless of the kind of the acidic solution. The genomic titer of rAAV6 before concentration was determined and the recovery rate was calculated in the same manner as Example 1-(6). As a result, the rAAV6 before concentration had an equal recovery rate regardless of the kind of the acidic solution. These results show that when sodium deoxycholate and an acidic solution are added to a mixture of rAAV and contaminating proteins, the contaminating proteins can be precipitated and removed by addition of any kind of acidic solution.

Example 6: Study of Various Kinds of Surfactants (1) Preparation of Extract of rAAV2

An extract of rAAV2 was prepared in the same manner as Example 3-(1) to (3).

(2) Formation and Removal of Precipitate by Addition of Various Kinds of Surfactants and Addition of Citric Acid To the rAAV2 extract obtained by Example 6-(1), 1/100 volume of 20 U/μL Cryonase (registered trademark) Cold-active Nuclease was added (final concentration: 0.2 U/μL), and then reacted at 37° C. for 1 hour. A part of the reaction sample was divided into 3 aliquots. To each sample, 1/10 volume of 5% (v/v) sodium deoxycholate, 5% (v/v) sodium chenodeoxycholate, or 5%. (v/v) sodium cholate was added, and after the sample was left to stand at 37° C. for minutes, 1/20 volume of 1 M citric acid was further added. Each sample was confirmed to be acidic by pH measurement. The conditions of each sample are shown in Table 6.

TABLE 6

| Sample | Surfactant | 1M citric acid |
|---|---|---|
| 1 | 1/10 volume 5% (v/v) sodium deoxycholate (final concentration 0.5% (v/v)) | 1/20 volume (final concentration 0.05M) |
| 2 | 1/10 volume 5% (v/v) sodium chenodeoxycholate (final concentration 0.5% (v/v)) | 1/20 volume (final concentration 0.05M) |
| 3 | 1/10 volume 5% (v/v) sodium cholate (final concentration 0.5% (v/v)) | 1/20 volume (final concentration 0.05M) |

In all the samples, a precipitate was formed. The sample was centrifuged at 5,000×g for 5 minute at 4° C., and a supernatant was collected to remove the precipitate. The collected supernatant was filtered with a 0.45 μm pore size filter to obtain a filtrate as rAAV2 before concentration.

(3) Purification and Concentration of rAAV2 by Ultrafiltration Membrane

The rAAV2 before concentration obtained by Example 6-(2) was put on a 100 kDaK ultrafiltration membrane, and centrifuged at 2,000×g for 5 minutes or more at 4° C. A filtrate was discarded. Further, "a series of operations (washing operation) wherein 14 mL of D-PBS was added onto the ultrafiltration membrane, suspended and centrifuged under the above-mentioned conditions, and a filtrate was discarded" was repeated 5 times to obtain a final concentrate as purified rAAV2. By this series of operations, contaminating substances having low molecular weight were removed and rAAV2 was concentrated.

(4) Determination of Purity of rAAV2

The purity of the rAAV2 extract (lane C), the rAAV2 before concentration (lane Pre), and the purified rAAV2 (lane F) was determined in the same manner as Example 1-(5). Results are shown in FIG. 5.

In FIG. 5, all bands found in lane C and lane Pre are bands corresponding to contaminating proteins. Since the concentration of rAAV2 at this stage is low, bands corresponding to rAAV are not detected. In contrast, 3 bold bands found in lane F are bands corresponding to structural proteins (VP1, VP2, VP3) of rAAV2. As seen from FIG. 5, regarding all surfactants, lane Pre had a low number of bands corresponding to contaminating proteins as compared with lane C. This result shows that the contaminating proteins can be precipitated and removed by addition of a surfactant and addition of citric acid regardless of the kind of the surfactant.

INDUSTRIAL APPLICABILITY

According to the method of producing a non-enveloped virus of the present invention, a non-enveloped virus particle with high purity can be obtained without laborious operations. A non-enveloped virus particle produced by the production method of the present invention and a composition comprising the non-enveloped virus particle as an active ingredient are very useful in gene transfer methods in the fields of basic research study and clinical application for gene therapy.

The invention claimed is:

1. A method of producing a non-enveloped virus particle, the method comprising:
    (a) a step of adding a carboxylic acid type anionic surfactant to a neutral or basic sample containing a non-enveloped virus particle,
    (b) a step of acidifying the sample to which the surfactant is added to form a precipitate,
    (c) a step of removing a precipitate formed in step (b) to obtain a supernatant fraction containing the non-enveloped virus particle,
  wherein the non-enveloped virus particle is adeno-associated virus particle.

2. The method according to claim 1, which further comprises (d) a step of purifying the non-enveloped virus after step (c).

3. The method according to claim 1, wherein the carboxylic acid type anionic surfactant is selected from the group consisting of sodium deoxycholate, sodium chenodeoxycholate, sodium cholate, sodium glycocholate, sodium taurocholate, and sodium taurodeoxycholate.

4. The method according to claim 1, wherein the step of acidifying is a step of adding an acidic solution.

5. The method according to claim 1, wherein the neutral or basic sample containing a non-enveloped virus particle is a lysate or a homogenate of a non-enveloped virus-producing cell, a culture supernatant of a non-enveloped virus-producing cell which contains a non-enveloped virus particle, or an extract obtained from a non-enveloped virus-producing cell.

6. The method according to claim 5, wherein the neutral or basic sample containing a non-enveloped virus particle is a sample obtained by bringing a non-enveloped virus-producing cell into contact with an acidic solution and then adjusting to a neutral or basic pH.

7. The method according to claim 1, wherein the neutral or basic sample containing a non-enveloped virus particle is a sample treated with nuclease.

8. A kit for performing the method according to claim 1, comprising:
    (1) a carboxylic acid type anionic surfactant, and
    (2) an acidic solution.

9. The kit according to claim 8, which further comprises a neutralizing solution.

* * * * *